(12) United States Patent
Springer et al.

(10) Patent No.: US 6,800,783 B2
(45) Date of Patent: Oct. 5, 2004

(54) METHOD FOR THE SYNTHESIS OF ALIPHATIC CARBOXYLIC ACIDS FROM ALDEHYDES

(75) Inventors: Helmut Springer, Dinslaken (DE); Peter Lappe, Dinslaken (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 10/204,619

(22) PCT Filed: Feb. 21, 2001

(86) PCT No.: PCT/EP01/01943
§ 371 (c)(1),
(2), (4) Date: Sep. 5, 2002

(87) PCT Pub. No.: WO01/66504
PCT Pub. Date: Sep. 13, 2001

(65) Prior Publication Data
US 2003/0078453 A1 Apr. 24, 2003

(30) Foreign Application Priority Data
Mar. 4, 2000 (DE) .......................... 100 10 771

(51) Int. Cl.⁷ .................. C07C 51/235; C07B 33/00
(52) U.S. Cl. .................. 562/531; 562/534; 554/137
(58) Field of Search .................. 562/531, 534; 554/137

(56) References Cited

U.S. PATENT DOCUMENTS

| | | | |
|---|---|---|---|
| 2,010,358 A | | 8/1935 | Groll et al. |
| 3,579,575 A | * | 5/1971 | Bouniot ...................... 562/531 |
| 4,013,691 A | | 3/1977 | Maki et al. |
| 4,285,875 A | * | 8/1981 | Cornils et al. ............... 562/531 |
| 4,487,720 A | * | 12/1984 | Fruchey ...................... 554/134 |
| 4,733,007 A | * | 3/1988 | Andrade et al. ............. 562/534 |

FOREIGN PATENT DOCUMENTS

| | | | |
|---|---|---|---|
| EP | 0682000 A | * | 11/1995 |
| GB | 706009 | | 3/1954 |
| GB | 1103885 | | 2/1968 |
| GB | 1565716 | | 4/1980 |

* cited by examiner

*Primary Examiner*—Ba K. Trinh
*Assistant Examiner*—Taylor Victor Oh
(74) *Attorney, Agent, or Firm*—Muserlian, Lucas and Mercanti

(57) ABSTRACT

The invention relates to a method for the synthesis of aliphatic carboxylic acids by the catalytic oxidation of aldehydes with oxygen, or oxygen-containing gas mixtures. Metals of groups 5 11 of the periodic table of elements, or the compounds thereof are used as catalyst, in amounts of up to 5 ppm, based upon the amount of aldehyde used.

12 Claims, No Drawings

METHOD FOR THE SYNTHESIS OF ALIPHATIC CARBOXYLIC ACIDS FROM ALDEHYDES

This application is a 371 of PCT/EP01/01943 filed Feb. 21, 2001.

The present invention relates to a novel, noncatalytic process for preparing aliphatic carboxylic acids from aldehydes by oxidation with oxygen or oxygen-containing gases.

Aldehydes are used on a large scale as starting materials for obtaining carboxylic acids. The preference for aldehydes for this use derives from their ready availability by a number of processes, which are also used in industry. Moreover, the carbonyl of the aldehydes can easily be converted into the carboxyl group characteristic of carboxylic acids. In processes applied industrially, the conversion of aldehydes to carboxylic acids often takes place in the presence of catalysts. However, there is no lack of warnings about employing catalysts because they promote the occurrence of side reactions, e.g. decarbonylation of the aldehydes employed to hydrocarbons. Accordingly, various processes in which the use of catalysts is dispensed with are also known. To avoid side reactions, both the catalytic and the noncatalytic processes employ temperatures which are as low as possible, and in general the reaction temperature does not exceed 100° C. Suitable catalysts are mainly salts of transition metals, in particular salts of cobalt and of manganese, and of chromium, iron, copper, nickel, silver and vanadium. Nevertheless, the formation of carboxylic acids from aldehydes is frequently associated, even if optimal temperature conditions are maintained, with side reactions and degradation reactions. This applies equally to reactions in the presence and in the absence of catalysts. In such cases, the selectivity of the conversion can be considerably improved by adding alkali metal salts of weak acids to the reactants. However, the disadvantage of this variant of the process is that the alkali metal salts have an inhibitory effect, so that long reaction times are necessary for complete conversion of the starting materials.

In the process described in DE-A 30 29 700, the appropriate aldehydes for preparing aliphatic monocarboxylic acids having 6 to 9 carbon atoms are oxidized with oxygen in pure form or with air. A combination of manganese and copper compounds which are soluble in the acid acts as catalyst. The metals are each present in an amount of about 10 to about 2000 ppm, preferably 200 to 600 ppm, manganese and copper, based on the weight of the liquid reaction mixture. The molar ratio of manganese to copper is from 5:1 to 0.5:1. The conversion of the starting materials takes place in liquid phase at temperatures of about 50 to 80° C. and pressures in the range from about 1.4 to 10.3 bar. The main difficulty of this process is described, in the description of the process, as being the presence of copper compounds, and manganese compounds, in the reaction product, i.e. in the carboxylic acid. Elaborate purification measures are necessary to remove the metals, for example precipitation thereof with aqueous oxalic acid.

The process disclosed in U.S. Pat. No. 4,487,720 for preparing $C_5$ to $C_9$ monocarboxylic acids by oxidizing aldehydes with the same number of carbon atoms using pure oxygen or air likewise operates with copper and manganese compounds as catalysts. The total amount of the metals extends over a range from 10 to 200 ppm, based on the total weight of the solution consisting of aldehyde, acid and catalyst. Manganese and copper are employed in a molar ratio of about 3:1 to about 1:1. The disadvantage described for this procedure is the formation of copper films which appear on purification of the acid by distillation and result in mechanical damage to the distillation apparatus. To avoid this problem, it is recommended that the distillation be carried out in the presence of oxygen.

Another catalytic process for reacting aldehydes with oxygen to form carboxylic acids is disclosed in the published international application WO 97/14668. The catalysts used are substituted or unsubstituted alkylamines, alkylamine N-oxides, aromatic amines, aromatic N-oxides, heterocyclic amines, heterocyclic amine N-oxides and mixtures thereof in an amount ranging from about 0.001 or less to about 10 or more mole equivalents, based on the aldehyde. About 0.005 to about 2 mole equivalents are preferably employed, in particular about 0.005 to about 1.2 mole equivalents of the amine or of the amine N-oxide, based on the aldehyde. It is expressly pointed out that the nitrogen compounds with catalytic activity must have a higher boiling point than the product of the reaction in order to suppress contamination of the acid by the catalyst.

According to the teaching of the published Japanese patent application 53-105413, α-branched aliphatic aldehydes are oxidized with oxygen in the presence of lithium or alkaline earth metal compounds, which are employed in amounts of from 0.01 to 10% by weight (based on the complete reaction system), in order to prepare α-branched aliphatic carboxylic acids.

The procedure described in the French patent application 2 769 624 is characterized by maintaining low reaction temperatures, namely temperatures between 0 and 25° C. The process likewise requires the presence of alkali metal or alkaline earth metal compounds as auxiliaries. It is not disclosed what specific effects these compounds display, i.e. whether they merely improve the selectivity of the conversion, as known, or else possibly also increase the rate of reaction at the chosen low temperatures.

The published German patent application 26 04 545 relates to the preparation of alkylcarboxylic acids of general formula $C_nH_{2n+1}COOH$, in which n has a value from 2 to 18, by hydroformylation of an olefin $C_nH_{2n}$ and direct oxidation of the reaction mixture resulting from the hydroformylation. Direct means in this connection that there is no previous workup of the hydroformylation product. The process is used in particular for preparing mixtures of isomeric $C_9$ to $C_{16}$ fatty acids. Suitable starting olefins are preferably dimers and trimers of propene and the butenes, including in particular the dimeric isobutene (2,4,4-trimethyl-1-pentene). Both individual reactions in the two-stage process, i.e. both the hydroformylation and the oxidation, are catalyzed by rhodium in the form of its compounds. The rhodium concentration in the reaction mixture subjected to the oxidation is therefore determined by the relatively high rhodium content in the hydroformylation product. In order to ensure that the overall process is economic, it is necessary to recover as completely as possible the noble metal from the final product of the process, the carboxylic acid, by suitable measures. In addition, it cannot be precluded that unwanted side reactions are favored by rhodium at the concentration present during the oxidation process, since the carboxylic acid yield is, as shown by the examples, inadequate for industrial exploitation of the process.

Larkin reports in J. Org. Chem. 1990, 55, pp. 1563 et seq. that the presence of catalysts in the commercially implemented oxidation of aldehydes to carboxylic acids is regarded as necessary because traces of metal salts are present in the reaction mixture and may catalyze the side reactions. The formation of the metal salts is attributed to corrosion of metallic parts of the system. The task of the catalysts is to overcompensate the effect of the corrosion products.

Ullmanns Encyclopädie der technischen Chemie, 4th edition 1972 et seq., volume 9, also refers to repeatedly to the adverse effect of metallic impurities in the initial aldehydes employed for the oxidation. Thus, for example, iron and cobalt salts dissolved in butyraldehyde lead, on oxidation thereof to butyric acid, to an increased production of by-products (loc. cit., page 142, left-hand column) and in the oxidation of 2-ethylhexanal to 2-ethylhexanoic acid the carbonylation of the initial aldehyde to heptane is promoted by heavy metal ions (loc. cit. page 144, left-hand column).

The known processes for preparing carboxylic acids from aldehydes do not yet meet to the full extent the requirements for modern processes used industrially. The use of catalysts often leads to undesired side reactions occurring. In addition, they also require elaborate purification steps, to which the product of the reaction must be subjected in order to obtain carboxylic acids which can be processed further without problems. Noncatalytic processes are frequently unsatisfactory in terms of the reaction rate and in relation to the conversion and selectivity for the required product.

The object therefore was to develop a procedure which combines the advantages of the noncatalytic oxidation of aldehydes to carboxylic acids, especially the absence of interfering foreign substances and the avoidance of side reactions, with the advantages of oxidation in the presence of catalysts, in particular an adequate reaction rate, but substantially precludes the disadvantages of each of the reactions. The desired result is to obtain carboxylic acids from aldehydes with acceptable technical complexity in high yield and purity.

This object is achieved by a process for preparing aliphatic carboxylic acids having 4 to 11 carbon atoms by oxidation of the corresponding aldehydes with oxygen or oxygen-containing gas mixtures at 20 to 100° C. The process comprises carrying out the oxidation of the aldehydes in the presence of from 0.1 to 5.0 ppm by weight of a metal of groups 5 to 11 of the Periodic Table of the Elements or the corresponding amount of a compound of such a metal or mixtures of such metals and/or metal compounds, based o the aldehyde employed with the proviso that the addition of polydentate ligands containing nitrogenous heterocycles shall be excluded.

It is surprisingly possible in the presence of small amounts of selected metals or compounds of these metals to convert aldehydes with pure oxygen or oxygen-containing gas mixtures with high conversion and very selectively into the corresponding carboxylic acids. The amounts of metals used, which are a maximum of 5 parts by weight per 1 million parts by weight of aldehyde, ensure a reaction rate which is sufficient also for industrial needs. However, they do not give rise to unwanted side reactions, so that the aldehydes are converted almost exclusively into the carboxylic acids corresponding to them. In addition, the amounts of metals employed are so low that there is no need to recover or remove them from the reaction product, either from the viewpoint of the economics of the process, e.g. on use of costly noble metals, or in view of the purity of the carboxylic acids which is required for various areas of application.

The catalyst added to the oxidation mixture according to the invention is at least one metal from groups 5 to 11 of the Periodic Table of the Elements (in the version of the IUPAC recommendation of 1985) or at least one compound of such a metal. If metals are used as catalysts, it advisable to add them in a fine dispersion to the reaction mixture in order to facilitate their conversion into the catalytically active form. This is because it can be assumed that the metal reacts with carboxylic acid, which is present in traces in the aldehyde, to form a salt which is soluble in the reaction mixture and acts catalytically. In place of the metals in elemental form it is also possible to use compounds of the metals as catalysts. The nature of the compounds is subject to no restriction in this connection. Unless special reasons apply, however, the preferred compounds will be those soluble in the reaction medium from the outset, in order to avoid the onset of the reaction being delayed by previous formation of a soluble and thus particularly active metal compound.

The metals of groups 5 to 11 which are catalytically active even in a very small amount include vanadium, chromium, molybdenum, iron, cobalt, nickel, ruthenium, rhodium, palladium, copper, preferably chromium, iron, nickel, rhodium and, especially, iron and rhodium. The compounds soluble in the reaction mixture which are used are salts, in particular salts of organic acids, with preference being given to carboxylates of the acids which are the result of the oxidation reaction. Other suitable compounds of the metals employed according to the invention are complex compounds, e.g. acetylacetonates, metal carbonyls, metal hydride-carbonyls, also carbonyl compounds which, besides carbon monoxide and, where appropriate, hydrogen, also contain other ligands, e.g. phosphines substituted by organic radicals, such as arylphosphines, alkylphosphines, arylalkylphosphines. One example of ligands of this type is triphenylphosphine.

It is not necessary to employ the catalytically active metals or the compounds containing catalytically active metals as pure substances. On the contrary, it is also possible to employ mixtures of said metals or metal compounds and, moreover, mixtures of metals and metal compounds as catalysts.

Besides the choice of the catalytic reactive metals, another very essential feature of the novel process is to maintain a maximum ratio by weight between catalyst and aldehyde to be oxidized. The upper limit of this ratio according to the invention is 5 ppm, i.e. 5 parts by weight of catalyst metal per $10^6$ parts by weight of aldehyde. It has proved particularly suitable to use from 0.2 to 3 parts by weight of catalyst metal, and preferably 0.5 to 2 parts by weight of catalyst metal, per $10^6$ parts by weight of aldehyde. The ratios between catalyst metal and aldehyde described above also apply on use of metal compounds, i.e. the amount of compound to be employed is determined by its metal content. This applies correspondingly on use of mixtures of various catalytically active metals or metal compounds and of mixtures of metals and metal compounds.

The process of the invention is carried out in the temperature range from 20 to 100° C. It is preferably carried out at between 20 and 80° C., in particular between 40 and 80° C. The temperature management, constant or variable temperature, can be adapted to the individual requirements of the starting material and to the reaction circumstances.

The reactants are preferably reacted under atmospheric pressure. The use of elevated pressure is not, however, precluded. The working range is normally from atmospheric pressure to 1.0 MPa, preferably atmospheric pressure to 0.8 MPa.

The reaction time needed to convert aldehydes into carboxylic acids by the process of the invention depends inter alia on the reaction temperature, the nature of the starting materials and the ratio of the amounts of the reactants. It is normally from 30 min to 20 h, in particular 3 to 8 h.

The novel process is centered on the oxidation of $C_4$ to $C_{11}$ aldehydes both unbranched and branched. The origin of the aldehydes is not restricted to particular preparation processes. Aldehydes obtained by oxo synthesis, i.e. by reacting $C_3$ to $C_{10}$ olefins with carbon monoxide and hydrogen, are preferred because of their ready availability. It is immaterial in this connection which specific embodiment of the oxo synthesis was used to obtain the aldehydes, i.e. whether the reaction was catalyzed, for example, by cobalt or by rhodium, whether the metals were employed alone or together with complexing agents, and the catalyst was homogeneously dissolved in the reaction mixture or formed a separate heterogeneous phase.

The oxidizing agent used in the process of the invention is molecular oxygen or gas mixtures containing molecular oxygen. Other constituents of such gas mixtures are inert gases, for example nitrogen, noble gases and carbon dioxide. The proportion of inert constituents in the oxygen-containing gas mixture is up to 90% by volume, in particular 30 to 80% by volume. The preferred oxidizing agents are oxygen or air.

The aldehydes can be employed as such or dissolved in a solvent which is inert under the reaction conditions. Examples of suitable solvents are ketones such as acetone, esters, for example ethyl acetate, hydro-carbons, for example toluene, and nitrohydrocarbons such as nitrobenzene. The concentration of the aldehyde is limited by its solubility in the solvent.

The process of the invention can be carried out batchwise or continuously. Recycling of unreacted reactants is possible in both cases.

In a proven embodiment of the process of the invention, the aldehyde is placed together with the catalyst in a suitable reactor, for example a tubular reactor which is provided with a distributor plate and optionally also contains packings, and the oxygen or the oxygen-containing gas mixture is passed upward through the aldehyde containing dissolved or suspended catalyst.

In another embodiment, the reactor used is a trickle tower containing packings. Aldehyde and catalyst are allowed to trickle down over the packing and, at the same time, oxygen or an oxygen-containing gas mixture is passed cocurrently or countercurrently into the tower.

The following examples describe the preparation of n-butyric acid, 2-methylbutyric acid, n-heptanoic acid and isononanoic acid by the claimed process. The reaction of the initial aldehydes takes place according to the invention in the presence of metals of groups 5 to 11 of the Periodic Table or compounds of these metals as catalysts. The examples are compared with the results of tests (comparative examples) in which aldehydes underwent noncatalytic oxidation. Comparative example 3 is an exception, describing the oxidation of 2-methylbutanal. Taking account of the characteristic property of α-branched aldehydes to undergo side reactions to a large extent during noncatalytic oxidation, this example made a comparison with the oxidation which is normally chosen by the skilled worker in the presence of an alkali metal salt. The results of the respective tests are indicated by stating the following characteristic variables:

GC analysis of the crude acid; the forerun component is not subdivided but combined under the designation low boilers;

aldehyde conversion;

selectivity; this is derived from the amount of carboxylic acid in the reaction product relative to reacted aldehyde.

The novel process is, of course, not confined to the embodiments described hereinafter.

EXAMPLES

Preparation of n-butyric Acid

Comparative Example 1

The liquid-phase oxidation of n-butanal to n-butyric acid was carried out without added catalyst in a glass bubble column reactor with an internal diameter of 38 mm and a length of 150 cm. Depending on the behavior of the reaction, external cooling or heating of the reactor was provided by a water circulation connected to a heat exchanger, and the internal temperature was kept constant in this way. The oxygen was fed in from below through a glass filter plate which had a maximum pore width of 16–40 μm and was connected to the bubble column.

In the oxidation, 800.0 g of aldehyde were employed. The results after oxidation at a constant 40° C. for 6 hours were as follows:

| GC analysis (%) | |
| --- | --- |
| Low boilers | 0.10 |
| n-Butanal | 2.76 |
| n-Butyric acid | 96.80 |
| Others | 0.34 |
| n-Butanal conversion (% of theory) | 96.6 |
| Selectivity for n-butyric acid (% of theory) | 99.6 |

Example 1

A solution of 44.6 g of toluene, 5.09 g of triphenylphosphine and 20 mg of rhodium (in the form of Rh 2-ethylhexanoate) in a 150 ml steel autoclave was treated with synthesis gas under a pressure of 27 MPa at 110° C. for 60 min. 2.7 g of the resulting solution with a rhodium content of 1.1 mg were mixed with 800.0 g of butanal and employed in the oxidation under the conditions of comparative example 1.

The results after oxidation at a constant 40° C. for 6 hours were as follows:

| GC analysis (%) | |
| --- | --- |
| Low boilers | 0.17 |
| Toluene | 0.25 |
| n-Butanal | 0.49 |
| n-Butyric acid | 98.82 |
| Others | 0.27 |
| n-Butanal conversion (% of theory) | 99.4 |
| Selectivity for n-butyric acid (% of theory) | 99.4 |

Preparation of 2-methylbutyric Acid

Comparative Example 2

The liquid-phase oxidation of 2-methylbutanal to 2-methylbutyric acid was carried out without added catalyst in a glass bubble column reactor with an internal diameter of 38 mm and a length of 150 cm. Depending on the behavior of the reaction, external cooling or heating of the reactor was provided by a water circulation connected to a heat exchanger, and the internal temperature was kept constant in this way. The oxygen was fed in from below through a glass filter plate which had a maximum pore width of 16–40 μm and was connected to the bubble column.

In the oxidation, 800.0 g of aldehyde were employed. The results after oxidation at a constant 50° C. for 6 hours were as follows:

| GC analysis (%) | |
| --- | --- |
| Low boilers | 0.79 |
| 2-Methylbutanal | 1.84 |
| 2-Methylbutyric acid | 85.53 |
| Others | 11.84 |
| 2-Methylbutanal conversion (% of theory) | 97.5 |
| Selectivity for 2-methylbutyric acid (% of theory) | 85.9 |

Comparative Example 3

800 g of 2-methylbutanal were employed together with a mixture of 75.3 g of 2-methylbutyric acid and 20.7 g of 50% by weight aqueous potassium hydroxide solution (equivalent to 2 mol % potassium, based on 2-methylbutanal) in the oxidation under the conditions of comparative example 2.

The results after oxidation at a constant 50° C. for 6 hours were as follows:

| GC analysis (%) | |
| --- | --- |
| Low boilers | 2.01 |
| 2-Methylbutanal | 2.45 |
| 2-Methylbutyric acid | 93.63 |
| Others | 1.91 |
| 2-Methylbutanal conversion (% of theory) | 96.5 |
| Selectivity for 2-methylbutyric acid (% of theory) | 95.0 |

Example 2

A solution of 44.0 g of toluene and 22 mg of rhodium (in the form of Rh 2-ethylhexanoate) in a 150 ml steel autoclave was treated with synthesis gas under a pressure of 27 MPa at 120° C. for 60 min. 3.81 g of the resulting solution with a rhodium content of 1.9 mg were mixed with 800.0 g of 2-methylbutanal and employed in the oxidation under the conditions of comparative example 3, i.e. in the presence of 75.3 g of 2-methylbutyric acid and 20.7 g of 50% by weight aqueous potassium hydroxide solution.

The results after oxidation at a constant 50° C. for 6 hours were as follows:

| GC analysis (%) | |
| --- | --- |
| Low boilers | 1.39 |
| Toluene | 0.43 |
| 2-Methylbutanal | 1.28 |
| 2-Methylbutyric acid | 94.38 |
| Others | 2.52 |
| 2-Methylbutanal conversion (% of theory) | 98.1 |
| Selectivity for 2-methylbutyric acid (% of theory) | 95.1 |

Example 3

800.0 g of 2-methylbutanal were employed together with a mixture of 75.3 g of 2-methylbutyric acid and 20.7 g of 50% by weight potassium hydroxide solution in the oxidation in analogy to comparative example 2. The methylbutyric acid contained, dissolved as salts, 0.10 mg of chromium, 0.07 mg of nickel and 0.47 mg of iron.

The results after oxidation at a constant 50° C. for 6 hours were as follows:

| GC analysis (%) | |
| --- | --- |
| Low boilers | 1.41 |
| 2-Methylbutanal | 1.17 |
| 2-Methylbutyric acid | 94.93 |
| Others | 2.49 |
| 2-Methylbutanal conversion (% of theory) | 98.3 |
| Selectivity for 2-methylbutyric acid (% of theory) | 95.3 |

Preparation of n-heptanoic Acid

Comparative Example 4

The liquid-phase oxidation of n-heptanal to n-heptanoic acid was carried out without added catalyst in a glass bubble column reactor with an internal diameter of 38 mm and a length of 150 cm. Depending on the behavior of the reaction, external cooling or heating of the reactor was provided by a water circulation connected to a heat exchanger, and the internal temperature was kept constant in this way. The oxygen was fed in from below through a glass filter plate which had a maximum pore width of 16–40 μm and was connected to the bubble column.

In the oxidation, 800.0 g of aldehyde were employed. The results after oxidation at a constant 50° C. for 6 hours were as follows:

| GC analysis (%) | |
| --- | --- |
| Low boilers | 0.82 |
| n-Heptanal | 5.42 |
| n-Heptanoic acid | 91.79 |
| Others | 1.97 |
| n-Heptanal conversion (% of theory) | 93.8 |
| Selectivity for n-heptanoic acid (% of theory) | 98.9 |

Example 4

A solution of 44.6 g of toluene, 5.09 g of triphenylphosphine and 20 mg of rhodium (in the form of Rh 2-ethylhexanoate) in a 150 ml steel autoclave was treated with synthesis gas under a pressure of 27 MPa at 110° C. for 60 min. 1.78 g of the resulting solution with a rhodium content of 0.7 mg were mixed with 800.0 g of n-heptanal and employed in the oxidation under the conditions of comparative example 4.

The results after oxidation at a constant 50° C. for 6 hours were as follows:

| GC analysis (%) | |
| --- | --- |
| Low boilers | 0.53 |
| Toluene | 0.26 |
| n-Heptanal | 2.28 |
| n-Heptanoic acid | 95.19 |
| Others | 1.74 |

-continued

| GC analysis (%) | |
|---|---|
| n-Heptanal conversion (% of theory) | 97.4 |
| Selectivity for n-heptanoic acid (% of theory) | 97.4 |

Example 5

A solution of 44.6 g of toluene and 20 mg of rhodium (in the form of Rh 2-ethylhexanoate) in a 150 ml steel autoclave was treated with synthesis gas under a pressure of 27 MPa at 110° C. for 60 min. 1.78 g of the resulting solution with a rhodium content of 0.8 mg were mixed with 800.0 g of n-heptanal and employed in the oxidation under the conditions of comparative example 4.

The results after oxidation at a constant 50° C. for 6 hours were as follows:

| GC analysis (%) | |
|---|---|
| Low boilers | 0.25 |
| Toluene | 0.25 |
| n-Heptanal | 1.99 |
| n-Heptanoic acid | 95.15 |
| Others | 2.36 |
| n-Heptanal conversion (% of theory) | 97.7 |
| Selectivity for n-heptanoic acid (% of theory) | 97.7 |

Preparation of Isononanoic Acid

Comparative Example 5

The liquid-phase oxidation of isononaldehyde to isononanoic acid was carried out without added catalyst in a glass bubble column reactor with an internal diameter of 38 mm and a length of 150 cm. Depending on the behavior of the reaction, external cooling or heating of the reactor was provided by a water circulation connected to a heat exchanger, and the internal temperature was kept constant in this way. The oxygen was fed in from below through a glass filter plate which had a maximum pore width of 16–40 µm and was connected to the bubble column.

In the oxidation, 800.0 g of aldehyde were employed. The results after oxidation at a constant 50° C. for 6 hours were as follows:

| GC analysis (%) | |
|---|---|
| Low boilers | 3.78 |
| Isononaldehyde | 8.46 |
| Isononanoic acid | 84.66 |
| Others | 3.10 |
| Isononaldehyde conversion (% of theory) | 90.0 |
| Selectivity for isononanoic acid (% of theory) | 99.9 |

Example 6

800.0g of isononaldehyde were mixed with a solution of 1.35 g of toluene and 0.6 mg of rhodium (in the form of Rh 2-ethylhexanoate) and employed in the oxidation under the conditions of comparative example 5.

The results after oxidation at a constant 50° C. for 6 hours were as follows:

| GC analysis (%) | |
|---|---|
| Low boilers | 4.19 |
| Toluene | 0.24 |
| Isononaldehyde | 1.65 |
| Isononanoic acid | 90.05 |
| Others | 3.87 |
| Isononaldehyde conversion (% of theory) | 98.0 |
| Selectivity for isononanoic acid (% of theory) | 98.4 |

What is claimed is:

1. A process for preparing aliphatic carboxylic acids having 4 to 11 carbon atoms by oxidation of the corresponding aldehydes with oxygen or oxygen-containing gas mixtures at 20 to 100° C., wherein the oxidation of the purified aldehydes takes place in the presence of 0.1 to 5.0 ppm by weight of a metal selected from the group consisting of vanadium, chromium, molybdenum, iron, cobalt, nickel, ruthenium, rhodium, palladium or copper or the corresponding amount of a compound of such a metal or mixtures of such metals and/or metal compounds, based on the aldehyde employed, with the proviso that the addition of polydentate ligands containing nitrogenous heterocycles shall be excluded.

2. The process of claim 1, wherein the oxidation of the aldehydes takes place in the presence of from 0.2 to 3 ppm of the metal or the corresponding amount of a compound of such a metal or mixtures of such metals and/or metal compounds, based on the aldehyde employed.

3. The process of claim 1, wherein the metal compounds are selected from the group consisting of carboxylates, acetylacetonates and carbonyl compounds.

4. The process of claim 3, wherein the metal carboxylates are salts of the carboxylic acids produced as the result of the oxidation of the aldehydes employed.

5. The process of claim 1, wherein the oxidation is carried out at temperatures in the range from 20 to 80° C.

6. The process of claim 1, wherein the oxidation is carried out under pressures in a range from atmospheric pressure to 1.0 Mpa.

7. The process of claim 1, wherein the oxygen-containing gas mixtures have a content of up to 90% by volume of inert gases.

8. The process of claim 2 wherein the amount of metal is 0.5 to 2 ppm.

9. The process of claim 1 wherein the metal is selected from the group consisting of chromium, iron, nickel and rhodium.

10. The process of claim 5 wherein the temperature is 40 to 80° C.

11. The process of claim 6, wherein the pressure is atmospheric pressure up to 0.8 Mpa.

12. The process of claim 7, wherein the gas mixture contains 30 to 80% by volume of inert gases.

* * * * *